(12) United States Patent
Ueno et al.

(10) Patent No.: US 8,449,456 B2
(45) Date of Patent: May 28, 2013

(54) ENDOSCOPE

(75) Inventors: Haruhiko Ueno, Akiruno (JP); Yuichi Ikeda, Tama (JP); Tomoaki Sato, Higashiyamato (JP); Shuji Nakamura, Akishima (JP)

(73) Assignee: Olympus Medical Systems Corp., Tokyo (JP)

( * ) Notice: Subject to any disclaimer, the term of this patent is extended or adjusted under 35 U.S.C. 154(b) by 1531 days.

(21) Appl. No.: 12/013,092

(22) Filed: Jan. 11, 2008

(65) Prior Publication Data

US 2008/0119695 A1 May 22, 2008

Related U.S. Application Data

(63) Continuation of application No. PCT/JP2006/314048, filed on Jul. 14, 2006.

(30) Foreign Application Priority Data

Jul. 14, 2005 (JP) ................................. 2005-205801

(51) Int. Cl.
*A61B 1/00* (2006.01)
*A61B 1/01* (2006.01)

(52) U.S. Cl.
USPC ........................... 600/146; 600/147; 600/148

(58) Field of Classification Search
USPC ................ 600/136, 145–152; 403/322.1, 361
See application file for complete search history.

(56) References Cited

U.S. PATENT DOCUMENTS

| | | | | |
|---|---|---|---|---|
| 2,975,785 A | * | 3/1961 | Sheldon | 600/141 |
| 4,878,112 A | * | 10/1989 | Ieoka | 600/109 |
| 7,780,593 B2 | * | 8/2010 | Ueno et al. | 600/146 |
| 2002/0103418 A1 | * | 8/2002 | Maeda et al. | 600/152 |
| 2002/0123664 A1 | | 9/2002 | Mitsumori | |
| 2004/0158203 A1 | * | 8/2004 | Cover et al. | 600/156 |
| 2009/0012365 A1 | * | 1/2009 | Ueno et al. | 600/146 |

FOREIGN PATENT DOCUMENTS

| | | |
|---|---|---|
| JP | 2-46820 | 2/1990 |
| JP | 4-82529 | 3/1992 |
| JP | 6-95008 | 4/1994 |
| JP | 6-105800 | 4/1994 |
| JP | 6-114001 | 4/1994 |
| JP | 6-64605 | 9/1994 |
| JP | 7-194608 | 8/1995 |
| JP | 2000-14628 | 1/2000 |
| JP | 2000-321034 | 11/2000 |

* cited by examiner

*Primary Examiner* — Matthew J Kasztejna
*Assistant Examiner* — Kevin G Barry, III
(74) *Attorney, Agent, or Firm* — Scully, Scott, Murphy & Presser, P.C.

(57) ABSTRACT

Lead screws and nut members screwed to the respective lead screws are provided on a wire operation section for operating wires for operating a bending section in a bending manner, and a driving force generating section, a drive coupling shaft rotationally driven in a spin direction by a driving force from the driving force generating section, and drive couplings are provided on a drive source unit separably coupled to the wire operation section. The lead screws are rotationally driven in a spin direction from the driving force generating section via the drive coupling shaft to move the nut members in the axial direction thereby performing pulling operation of the wires during coupling of the drive source unit and the wire operation section.

10 Claims, 10 Drawing Sheets

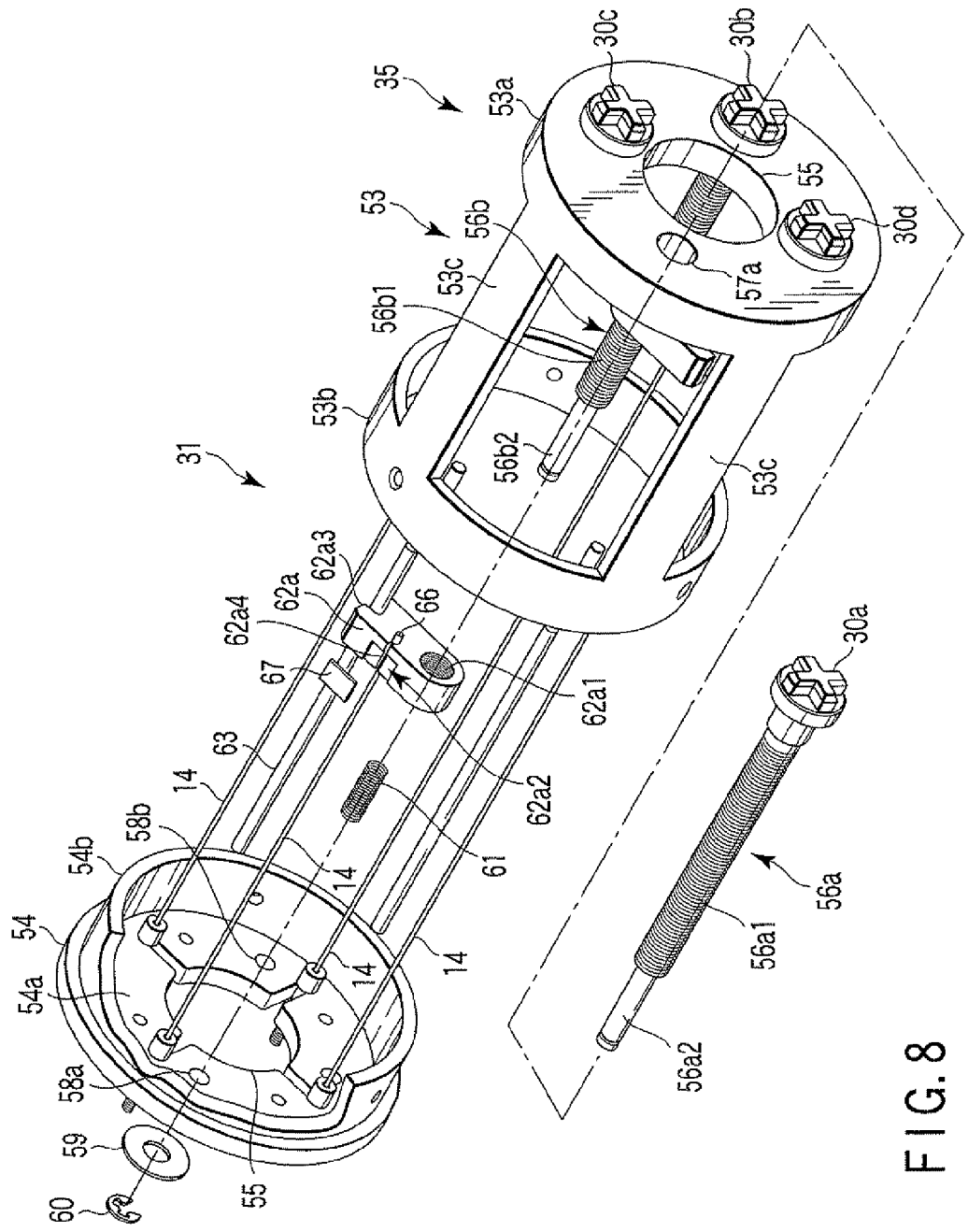
F I G. 8

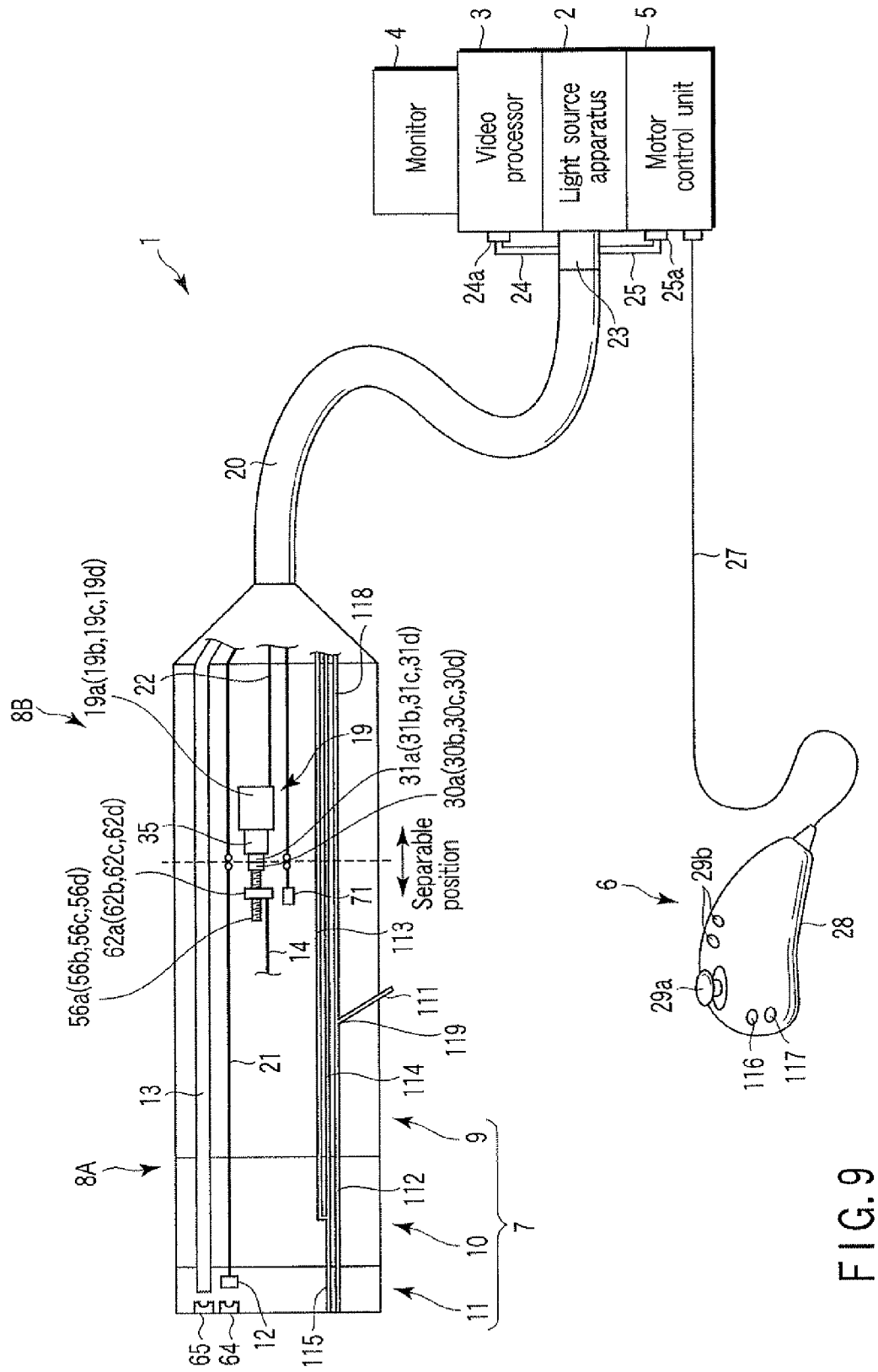
F I G. 9

ENDOSCOPE

CROSS REFERENCE TO RELATED APPLICATIONS

This is a Continuation Application of PCT Application No. PCT/JP2006/314048, filed Jul. 14, 2006, which was published under PCT Article 21(2) in Japanese.

This application is based upon and claims the benefit of priority from prior Japanese Patent Application No. 2005-205801, filed Jul. 14, 2005, the entire contents of which are incorporated herein by reference.

BACKGROUND OF THE INVENTION

1. Field of the Invention

The present invention relates to an endoscope of a drive source unit separable type that is provided with a drive source unit separably coupled to a distal end section of an insertion section of the endoscope via a separable section, where drive force generating means for operating a bending section disposed on a distal end side of the insertion section in a bending manner is incorporated in the drive source unit.

2. Description of the Related Art

Jpn. Pat. Appln. KOKAI Publications No. 2000-14628 (Patent Document 1) discloses one example of endoscope apparatus of a separable type. In the endoscope apparatus of a separable type, an insertion section of an endoscope and an operation section on a near side disposed at a proximal end section of the insertion section are separably coupled to each other via a separable section. The insertion section of the endoscope includes a bending section deformable in a bending manner disposed between a section comprising a slender soft section and a distal end section thereof. An operation knob of a bending operation mechanism for operating the bending section in a bending manner is provided on the operation section.

Distal end sections of four wire cables for performing a bending operation are fixed to a distal end section of the bending section. Proximal end sections of the wire cables extend toward the proximal end section of the insertion section. A transmission mechanism for transmitting a driving force to be transmitted from the operation knob to the bending section is disposed on the proximal end section of the insertion section. The transmission mechanism includes guide wheels reversing directions of the four wire cables and passive shafts. Proximal end sections of the wire cables are coupled to the passive shafts via the guide wheels.

A pinion is fixed to a drive shaft of the operation knob of the operation section. A pair of racks meshes with the pinion such that the racks face each other, and the drive shaft is provided in its state coupled to the racks. Such a configuration is adopted that, when the proximal end section of the insertion section of the endoscope and the operation section are coupled to each other via a separable section, the drive shaft and the passive shaft are caused to abut on each other, so that bending operation is performed according to advancing and retreating of the passive shaft.

Jpn. Pat. Appln. KOKAI Publications No. H6-114001 (Patent Document 2) discloses an endoscope apparatus having a configuration where a bending-drive source for driving a bending section of an endoscope is provided separately from a main body of the endoscope, and the endoscope and the bending-drive source are separably coupled to each other. Here, a driving force orthogonally-converting mechanism utilizing a bevel gear is provided in the endoscope. Further, an input shaft on the side of the endoscope and an output shaft on the side of the bending-drive source are separably coupled in a coaxial manner. Bending operation of the bending section of the endoscope is performed by a driving force from the bending-drive source during a coupling between the endoscope and the bending-drive source.

BRIEF SUMMARY OF THE INVENTION

According to a first aspect of the present invention, an endoscope comprising: a scope section provided with a slender insertion section which includes a distal end section and a proximal end section and is constituted to be inserted into a body cavity; a drive source unit separably coupled to the scope section, wherein the scope section includes a coupling end section separably coupled to the drive source unit at the proximal end section of the insertion section; the insertion section includes a bending section configured by coupling a plurality of bending pieces, a wire for operating the bending section in a bending manner which includes a distal end section and a proximal end section, where the distal end section is connected to the bending section and the proximal end section extends toward the proximal end section of the insertion section, and a wire operation section provided on the coupling end section; the wire operation section is provided with a screw member including a distal end section and a proximal end section and supported rotatably in a spin direction, and a responding member which includes a screw hole section screwed with the screw member and a wire connecting section connected to the proximal end section of the wire and moves in axial direction of the screw member according to rotation of the screw member; and the drive source unit is provided with driving force generating means which is separably coupled to the wire operation section and generates a driving force for bending the bending section, a drive shaft body which includes a distal end section and a proximal end section, and is rotationally driven in a spin direction by a driving force from the driving force generating means, and activating means which is disposed at the distal end section of the drive shaft body, includes a coupling section separably coupled to the proximal end section of the screw member at a coupling time of the drive source unit and the wire operation section, and rotationally drives the screw member in a spin direction in response to action of the drive shaft body rotationally driven in the spin direction by a driving force from the driving force generating means at the coupling time of the drive source unit and the wire operation section.

Preferably, the bending section is configured to be operable in four directions of up, down, left, and right in a bending manner, and the wire includes a pair of up and down direction wires for up and down bending operations for operating the bending section in up and down directions and a pair of left and right direction wires for left and right bending operations for operating the bending section in left and right directions.

Preferably, at least one of the proximal end section of the screw member and the coupling section of the drive shaft body includes a non-circular engagement projecting section and the other thereof includes an engagement recess section separably engaged with the engagement projecting section.

Preferably, the wire operation section is provided with detecting means for detecting advance and retreat of the responding member.

Preferably, the screw member includes a passive coupling provided on the proximal end section so as to be exposed from the coupling end section, and the coupling section includes a drive coupling section which is engaged with the passive coupling section in an axial direction to perform transmission of a driving force.

Preferably, the drive coupling section includes a drive coupling shaft and a drive coupling cylinder, and the drive coupling cylinder is provided with a biasing spring for biasing the drive coupling cylinder in a distal end direction thereof interposed between the drive coupling cylinder and the drive coupling shaft.

Preferably, the detecting means is one of a photo-reflector which detects a position of a reflecting member provided on the responding member and a photo-interrupter which detects a position of a projection provided on the responding member.

Preferably, a set of two the screw members for operating the up and down direction wires and a set of two the screw members for operating the left and right direction wires are each driven by one drive source.

Preferably, the screw member includes a gear section provided on the proximal end section so as to be exposed from the coupling end section; the coupling end section includes a first drive gear meshing with the gear section of the set of two the screw members for operating the up and down direction wires, a second drive gear meshing with the gear section of the set of two the screw members for operating the left and right direction wires, and passive couplings provided on the first drive gear and the second drive gear, spectively; and the drive source unit includes a drive coupling section engaged with the passive coupling of the first drive gear and the passive coupling of the second drive gear, respectively, to perform transmission of a driving force.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 8 is an exploded perspective view showing an internal structure of a wire operation section of the scope section of the separable-type endoscope according to the first embodiment;

FIG. 9 is a schematic configuration diagram of a whole system of a separable-type endoscope according to a second embodiment of the present invention;

DETAILED DESCRIPTION OF THE INVENTION

Figure 1:
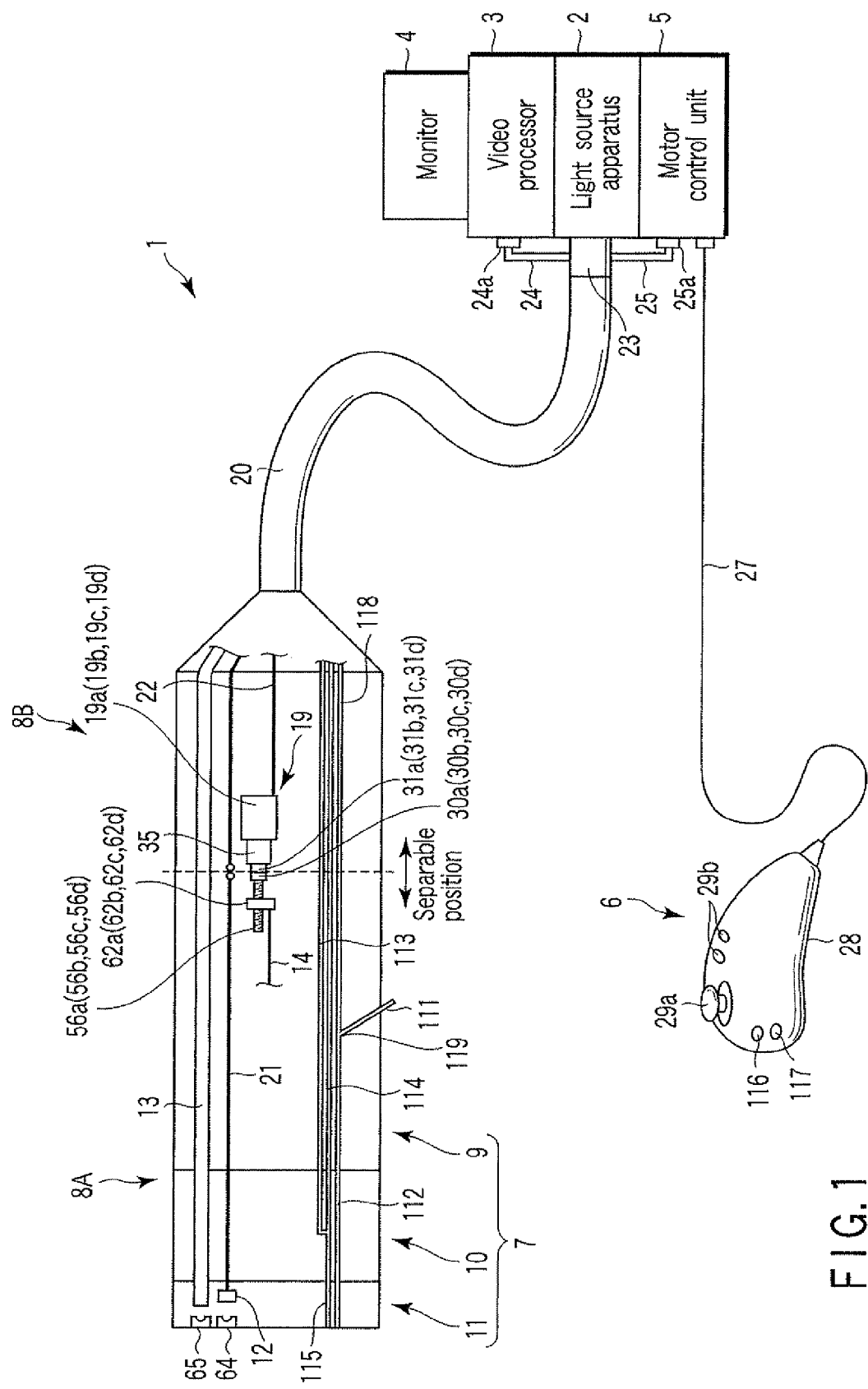
FIG. 1 is a schematic configuration diagram of a whole system of a separable-type endoscope according to a first embodiment of the present invention.

A first embodiment of the present invention will be explained below with reference to FIGS. 1 to 8. FIG. 1 is a schematic configuration diagram of a whole system of an endoscope according to the present embodiment. The endoscope system is provided with a separable-type endoscope 1, a light source apparatus 2, a video processor 3, a monitor 4, a motor control unit 5, and an operation section 6 that is an input apparatus for operation of the endoscope 1.

Figure 2:
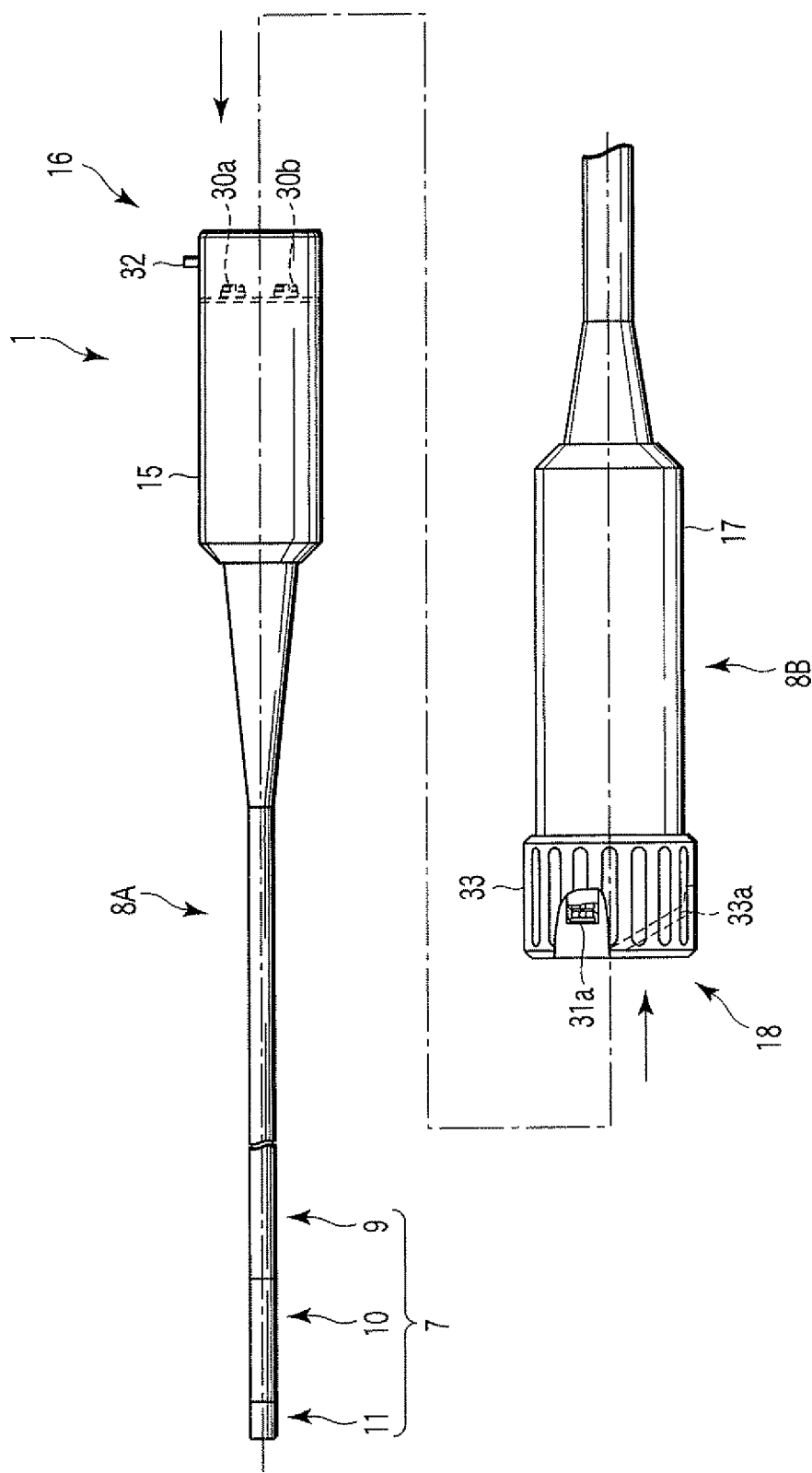
FIG. 2 is a side view showing a state that a proximal end side coupling section of a scope section and a drive source unit in the separable-type endoscope according to the first embodiment have been separated from each other.

FIG. 2 shows the separable-type endoscope 1. The separable-type endoscope 1 includes a scope section 8A and a drive source unit 8B. The scope section 8A is provided with a slender insertion section 7 that is constituted to be inserted into a body cavity. The drive source unit 8B is separably coupled to the scope section 8A.

The insertion section 7 of the scope section 8A includes a slender insertion pipe section 9, a bending section 10 deformable in a bending manner, and a hard distal end configuration section 11. The insertion pipe section 9 may be formed from a hard pipe section such as a metal pipe or a flexible pipe section. The bending section 10 is coupled to a distal end of the insertion pipe section 9. The distal end configuration section 11 is coupled to a distal end of the bending section 10.

An objective lens 64, an imaging apparatus such as a CCD 12 (see FIG. 1) for performing photoelectric conversion of an image imaged by the objective lens 64, an illumination lens 65, a distal end section of a light guide fiber 13 for guiding illumination light, and the like are incorporated in the distal end configuration section 11. Further, an opening section of a gas supply/water supply pipe conduit 115 (described later) incorporated in the insertion section 7, a distal end opening section of a procedure tool insertion pipe conduit 112 described later, and the like are provided on a distal end face of the distal end configuration section 11. In the bending section 10, a plurality of approximately ring-like bending pieces are arranged along an axial direction of the insertion section 7 and they are rotatably coupled to one another via rotating pins such as rivets.

The bending section 10 is connected with distal end side of four wires 14 (see FIG. 8) for bending operation to operate the bending section 10 in, for example, four directions of up, down, left, and right in a bending manner. Proximal end sections of each wire 14 extend toward the proximal end section of the insertion section 7.

A large-diameter section (coupling section) 15 larger in diameter than a major part of the insertion pipe section 9 is provided on the side of the proximal end of the insertion pipe section 9. A coupling end section 16 of the scope section 8A separably coupled with the drive source unit 8B is provided on a terminal end section of the large-diameter section 15.

Further, a procedure tool insertion section 111 is provided in the large-diameter section 15 on the side of the proximal end section of the scope section 8A in a projecting manner. A procedure tool insertion pipe conduit 112 that also serves as a suction pipe conduit, a water supply pipe conduit 113, and a gas supply pipe conduit 114 are provided inside the scope section 8A. A distal end section of the water supply pipe conduit 113 is coupled with a distal end section of the gas supply pipe conduit 114. A gas supply/water supply pipe conduit 115 is formed ahead of a coupling section of the water supply pipe conduit 113 and the gas supply pipe conduit 114. Further, a proximal end section of the procedure tool insertion pipe conduit 112 communicates with the procedure tool insertion section 111.

Incidentally, the procedure tool insertion pipe conduit 112 in which a procedure tool is inserted via the procedure tool insertion section 111 is also used as a channel for a sucked matter when suction is conducted. The procedure tool insertion pipe conduit 112 is coupled to a suction pipe conduit 118 provided as another member via a branched section 119. A sucked matter can be sucked into the suction pipe conduit 118 from the procedure tool insertion pipe conduit 112 via the branched section 119.

The drive source unit 8B is provided with a unit main body 17 with a diameter approximately equal to that of the large-diameter section 15 of the scope section 8A. A coupling end section 18 of the drive source unit 8B separably coupled to the coupling end section 16 of the scope section 8A is provided at a distal end section of the unit main body 17. Further, driving force generating means 19 generating a driving force for bending the bending section 10 is disposed inside the unit main body 17. The driving force generating means 19 includes four drive motors 19a, 19b, 19c, and 19d (described later) for bending operation to operate the bending section 10 in, for example, four directions of up, down, left, and right in a bending manner. Here, two drive motors 19a and 19b function as drive sources for operating the bending section 10 in, for example, the up and down directions in a bending manner. The other two drive motors 19c and 19d function as drive sources for operating the bending section 10 in the left and right directions in a bending manner.

A distal end section of a universal cable 20 is connected to a proximal end section of the unit main body 17 of the drive source unit 8B. A CCD cable 21, a plurality of electric cables, a light guide fiber 13, and the like are incorporated in the universal cable 20. The CCD cable 21 transmits a video signal from the CCD 12. The plurality of electric cables include motor cables 22 for power supply to the respective drive motors 19a to 19d in the driving force generating means 19, and the like.

A connector 23 separably coupled to the light source apparatus 2 is disposed at a proximal end section of the universal cable 20. Illumination light emitted from the light source apparatus 2 is supplied to the scope section 8A via the light guide fiber 13.

The connector 23 is connected with a video cable 24 and a motor cable 25. The video cable 24 is connected to the CCD cable 21. The motor cable 25 is connected to the motor cable 22. The video cable 24 is separably connected to the video processor 3 via a video connector 24a. Further, the motor cable 25 is separably connected to the motor control unit 5 via an electric connector 25a. The video processor 3 is connected to the monitor 4. An observation image of the scope section 8A picked up by the CCD 12 is converted to an electric signal. An output signal from the CCD 12 is input to the video processor 3 via the CCD cable 21 and the video cable 24. An output signal processed by the video processor 3 is then transmitted to the monitor 4. The observation image of the scope section 3A is displayed on a screen of the monitor 4.

The motor control unit 5 is connected with the operation section 6 for operating the endoscope 1 via a cable 27. The operation section 6 includes a hand piece 28 which a user can operate in one hand approximately in the same manner as a mouse for a personal computer. A joystick 29a for remotely operating the bending section 10 in a bending manner, a gas supply/water supply operation button 116, a suction button 117, a plurality of remote switches 29b other than the joystick and the buttons, and the like are disposed on the hand piece 28.

Figure 3:
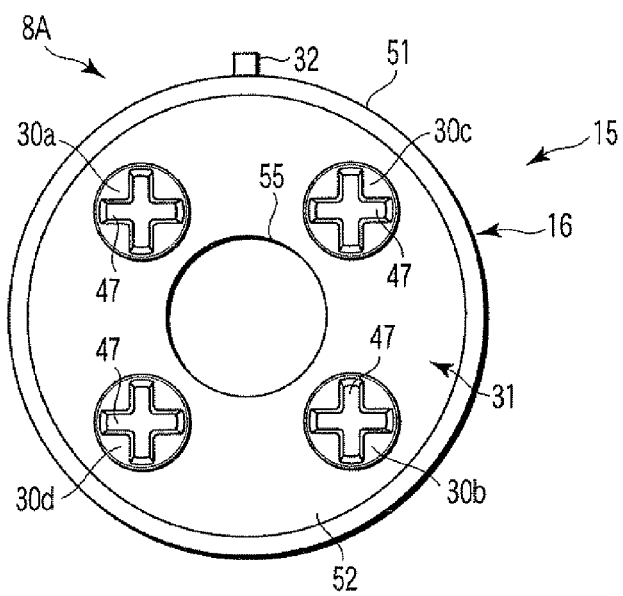
FIG. 3 is a front view of a coupling end section of the scope section of the separable-type endoscope according to the first embodiment.
Figure 4:
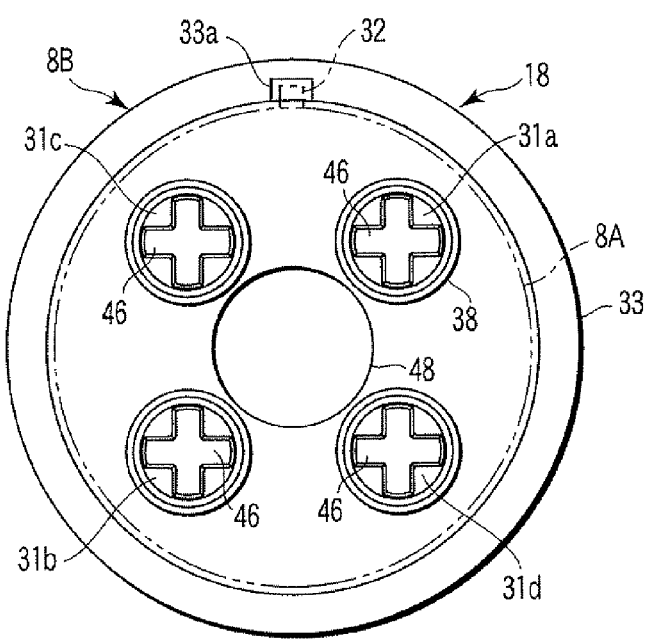
FIG. 4 is a front view of a coupling end section of the drive source unit of the separable-type endoscope according to the first embodiment.

FIG. 3 shows an end face of the coupling end section 16 of the scope section 8A, and FIG. 4 shows an end face of the coupling end section 18 of the drive source unit 8B. Four passive coupling sections 30a, 30b, 30c, and 30d corresponding to the bending operation directions of operating the bending section 10 in the bending manner, for example, four directions of up, down, left, and right are disposed on the end face of the coupling end section 16 of the scope section 8A. Here, the passive coupling sections 30a and 30b correspond to the bending operation directions of operating the bending section 10 in the up and down directions, while the passive coupling sections 30c and 30d correspond to the bending operation directions of operating the bending section 10 in the left and the right directions.

Further, four drive couplings 31a, 31b, 31c, and 31d corresponding to the respective bending operation directions of operating the bending section 10 in the bending manner, for example, four directions of up, down, left, and right are disposed on the end face of the coupling end section 18 of the drive source unit 8B. Here, the drive couplings 31a and 31b correspond to the bending operation directions of operating the bending section 10 in the up and down directions, while the drive couplings 31c and 31d correspond to the bending operation directions of operating the bending section 10 in the left and the right directions. The four drive couplings 31a, 31b, 31c, and 31d are disposed at positions corresponding to the four passive coupling sections 30a, 30b, 30c, and 30d, respectively.

An engagement pin 32 for an attaching and detaching mechanism is provided on a proximal end outer peripheral section of the large-diameter section 15 of the coupling end section 16 of the scope section 8A in a protruding manner. Further, a lock ring 33 coupled to the coupling end section 16 of the scope section 8A in a detachable manner is provided on the coupling end section 18 of the drive source unit 8B. The lock ring 33 is rotatably supported on the coupling end section 18 of the drive source unit 8B in the spin direction.

For example, a cam groove 33a which is engaged with the engagement pin 32 on the coupling end section 16 of the scope section 8A in a detachable manner is formed on an inner peripheral face of the lock ring 33. The coupling end section 16 of the scope section 8A and the coupling end section 18 of the drive source unit 8B are caused to abut on each other at a coupling time of the scope section 8A and the drive source unit 8B. At this time, the engagement pin 32 on the side of the scope section 8A is caused to engage the cam groove 33a of the drive source unit 8A in a state that the former has been inserted into the latter. In this state, the engagement pin 32 is moved to a lock position at a terminal end of the cam groove 33a by rotating the lock ring 33 by a desired rotational angle so that the scope section 8A and the drive source unit 8B are locked to each other in a coupled state.

Figure 5:
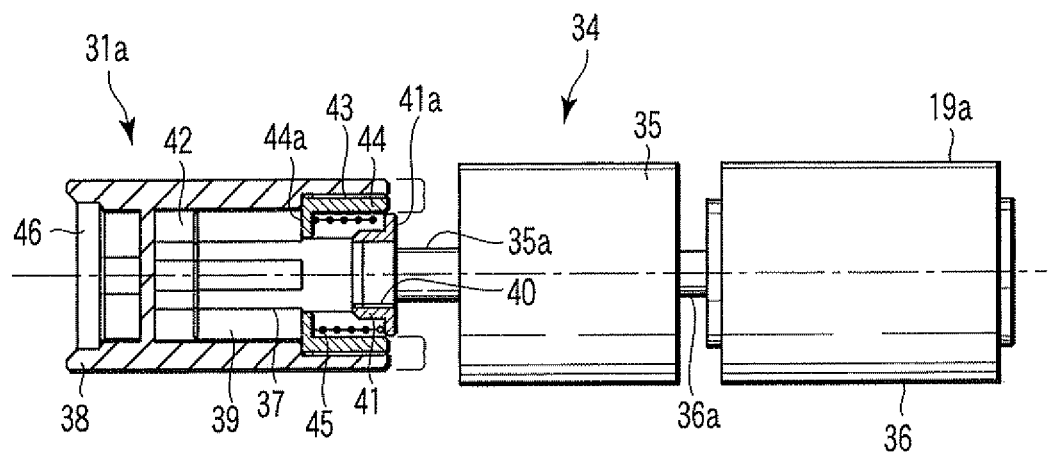
FIG. 5 is a side view showing a coupled state between drive couplings between the proximal end side coupling section of the scope section and the drive source unit in the separable-type endoscope according to the first embodiment in a partially sectioned manner.

FIG. 5 shows a motor-assembled unit (activating means) 34 where one drive motor 19a of four drive motors 19a, 19b, 19c, and 19d corresponding to the up, down, left, and right directions and configuring the driving force generating means 19 incorporated into the drive source unit 8B is assembled. Incidentally, all of the motor-assembled units 34 of the respective drive motors 19a, 19b, 19c, and 19d corresponding to the four directions of operating the bending section 10 in the up, down, left, and right directions in the bending manner have the same configuration. Therefore, here, only the configuration of the motor-assembled unit 34 for the drive motor 19a is explained and explanation of the motor-assembled units for the remaining drive motors 19b, 19c, and 19d are omitted.

The motor-assembled unit 34 for the drive motor 19a is configured so as to include a driving coupling (coupling section) 31a, a universal joint 35, and a motor unit 36. For example, a reduction gear mechanism including a planet gear is incorporated into the motor unit 36. An output shaft 36a of the motor unit 36 is coupled to the drive coupling 31a via the universal joint 35. The universal joint 35 includes a function of absorbing axial deviation of the drive coupling 31a and the passive coupling section 30a during coupling of the both.

Figure 6A:
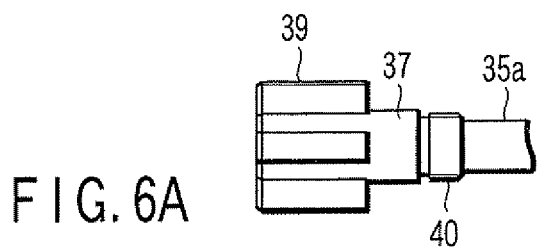
FIG. 6A is a side view showing a drive coupling shaft of the drive source unit in the separable-type endoscope according to the first embodiment.
Figure 6B:
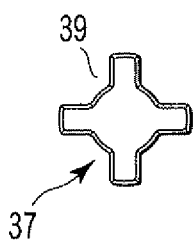
FIG. 6B is a front view of the drive coupling shaft shown in FIG. 6A.

The drive coupling 31a includes a drive coupling shaft (drive shaft body) 37 and a drive coupling cylinder 38. As shown in FIG. 5, a proximal end section of the drive coupling shaft 37 is fixed to a distal end of an output shaft 35a of the universal joint 35. A distal end section of the drive coupling shaft 37 is formed with a cross-shaped coupling section 39 with an approximately cross shape, as shown in FIGS. 6A and 6B.

Further, a male screw section 40 is formed on a proximal end section of the drive coupling shaft 37 near a fixing section with the output shaft 35a of the universal joint 35. The male screw section 40 is screwed with a first spring retainer 41 with an approximately cylindrical shape. A spring receiver 41a with a flange shape is formed on a proximal end section outer peripheral face of the first spring retainer 41.

As shown in FIG. 5, a fitting groove 42 fitted with the cross-shaped coupling section 39 of the drive coupling shaft 37 is formed in an inner cylindrical face of the drive coupling cylinder 38. The fitting groove 42 of the drive coupling cylinder 38 is formed to be approximately analogous to the cross-shaped coupling section 39 of the drive coupling shaft 37 and be slightly larger than the cross-shaped coupling section 39 of the drive coupling shaft 37. Thereby, a slight clearance is formed between the fitting groove 42 of the drive coupling cylinder 38 and the cross-shaped coupling section 39 of the drive coupling shaft 37 during coupling of the fitting groove 42 of the drive coupling cylinder 38 and the cross-shaped coupling section 39 of the drive coupling shaft 37.

Therefore, the drive coupling cylinder 38 and the drive coupling shaft 37 are coupled to each other so as to be slidable along a fitted section of the fitting groove 42 of the drive coupling cylinder 38 and the cross-shaped coupling section 39 of the drive coupling shaft 37 in an axial direction and allow transmission of a rotational driving force.

Further, a circular screw hole section 43 is formed in a cylindrical inner face of the drive coupling cylinder 38 on side of the proximal end section. A second spring retainer 44 with a cylindrical shape is screwed and fixed in the screw hole section 43. A flange-shaped spring receiver 44a projecting inwardly is formed on a distal end outer peripheral face of the second spring retainer 44.

A biasing spring 45 with a coil spring shape biasing the drive coupling cylinder 38 in a direction of a distal end side (the passive coupling section 30a) is interposed between the drive coupling cylinder 38 and the drive coupling shaft 37. The biasing spring 45 is fixed so as to be sandwiched between the spring receiver 44a of the second spring retainer 44 or the first spring retainer 41 screwed to the male screw section 40 of the drive coupling shaft 37 by the first spring retainer 41.

As shown in FIG. 4, cross-shaped recess sections 46 are formed at a distal end section of the drive coupling cylinder 38 by cross-shaped recessed sections. The cross-shaped recess section 46 is formed to be approximately analogous to a cross-shaped projecting section 47 (see FIG. 3) of a passive coupling section 30a and be slightly larger than the cross-shaped projecting section 47 of the passive coupling section 30a. Thereby, a slight clearance is formed between the cross-shaped recess section 46 of the drive coupling 31a and the cross-shaped projecting section 47 of the passive coupling section 30a during coupling of the cross-shaped recess section 46 of the drive coupling 31a and the cross-shaped projecting section 47 of the passive coupling section 30a. The drive coupling 31a and the passive coupling section 30a is engaged with each other in a detachable manner in a state the cross-shaped projecting section 47 of the passive coupling section 30a is inserted into the cross-shaped recess section 46 of the drive coupling 31a during coupling of the drive coupling 31a and the passive coupling section 30a so that transmission of a driving force is performed.

Incidentally, since such a state is normally maintained by a spring force of the biasing spring 45 that an end face of the spring receiver 44a of the second spring retainer 44 of the drive coupling cylinder 38 abuts on an end face of the cross-shaped coupling section 39 of the drive coupling shaft 37, the drive coupling cylinder 38 does not move toward the drive motor 19a from a normal state shown in FIG. 5. However, when the positions of the cross-shaped projecting section 47 and the cross-shaped recess section 46 do not aligned with each other at a connecting time of the drive coupling 31a and the passive coupling section 30a, the coupling end section 16 of the scope section 8A and the coupling end section 18 of the drive source unit 8B are connected to each other in a state that the drive coupling 31a has been once retreated toward the drive motor 19a, and when the positions of the cross-shaped projecting section 47 and the cross-shaped recess section 46 have aligned with each other according to rotation of the drive motor 19a following thereafter, the drive coupling cylinder 38 is pushed out in a direction of the passive coupling section 30a by the biasing spring 45 so that both the members are connected to each other.

The four drive couplings 31a, 31b, 31c, and 31d comprised above are disposed along a circumferential direction at equal intervals inside the lock ring 33 at the distal end section of the unit main body 17 of the drive source unit 8B. Further, a circular hole 48 is formed inside the four drive couplings 31a, 31b, 31c and 31d on the end face of the distal end section of the unit main body 17. The light guide fiber 13, the CCD cable 21, the water supply pipe conduit 113, the gas supply pipe conduit 114, the suction pipe conduit 118, and the like received in the insertion section 7 are disposed in the circular hole 48.

Figure 7:
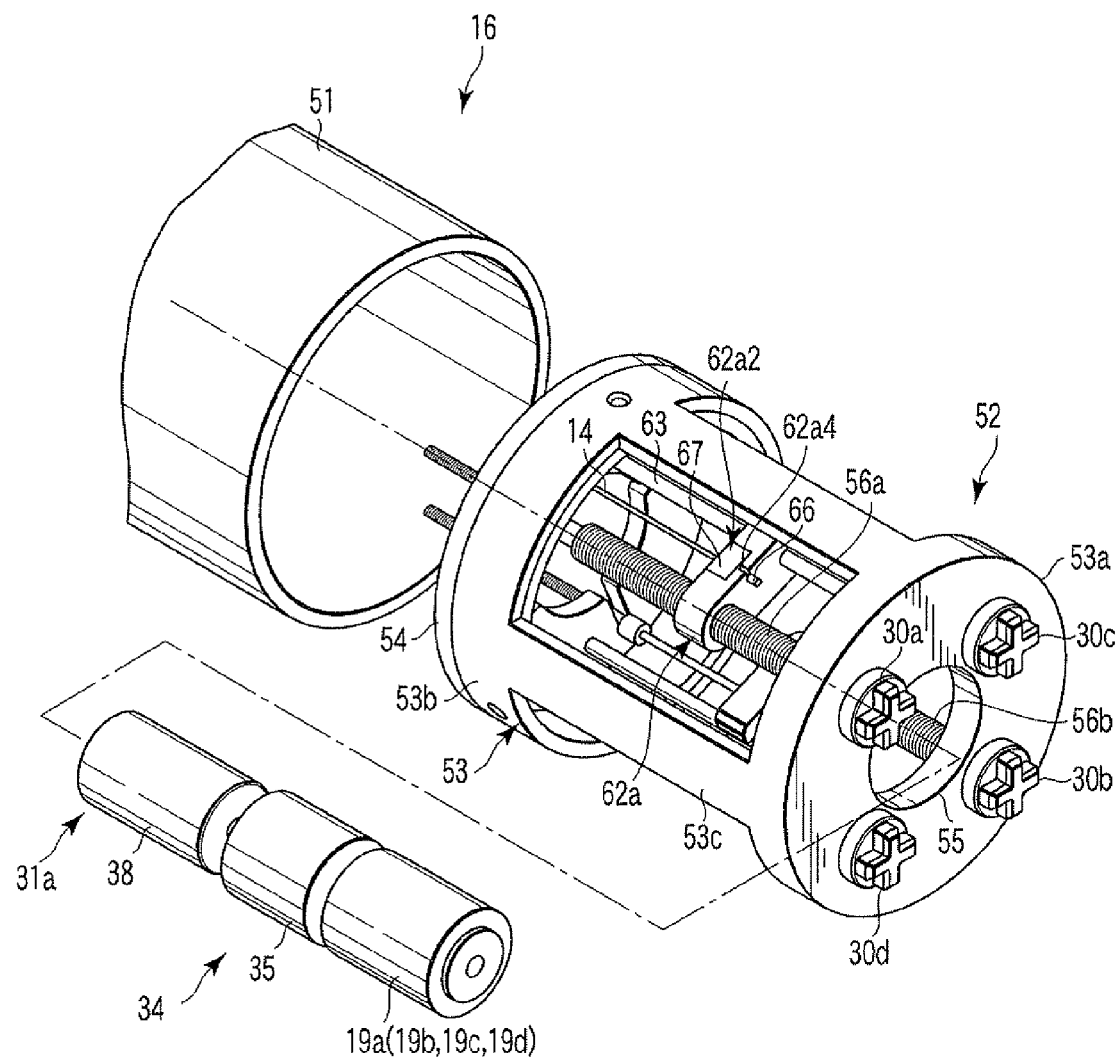
FIG. 7 is a perspective view of a main section showing an internal structure of a large-diameter section in the scope section of the separable-type endoscope according to the first embodiment.

FIG. 7 shows the internal configuration of the large-diameter section 15 in the scope section 8A. A cylindrical cover 51 and a wire operation section 52 attached in a state that it has been inserted into the cover 51 are provided to the large-diameter section 15 of the scope section 8A. The wire operation section 52 comprises power transmitting means for transmitting a driving force of the bending section 10 supplied from the drive source unit 8B as a pulling force of the wire 14 for bending operation.

FIG. 8 is an exploded perspective view of the wire operation section 52. The wire operation section 52 is provided with two (first and second) frame members 53 and 54 separably coupled to each other. The first frame member 53 is provided with a disc-shaped end plate 53a, a rear section ring 53b, and a plurality of (four, in this embodiment) arm-shaped coupling frames (beam sections) 53c. The disc-shaped end plate 53a and the rear section ring 53b are disposed so as to be spaced from each other in a centerline direction and face each other, and four coupling frames 53c are disposed between the disc-shaped end plate 53a and the rear section ring 53b.

The second frame member 54 is provided with a disc-shaped end plate 54a and a cylindrical coupling ring 54b. The second frame member 54 is coupled to the first frame member 53 in a state that the rear section ring 53b is fitted on the coupling ring 54b of the second frame member 54.

Further, the end plate 53a of the first frame member 53 and the end plate 54a of the second frame member 54 are formed at their centers with circular holes 55, respectively. The light guide fiber 13, the CCD cable 21, the water supply pipe conduit 113, the gas supply pipe conduit 114, the suction pipe conduit 118, and the like incorporated in the insertion section 7 are inserted in the circular holes 55.

(Since the embodiment includes four bending directions, four) lead screws (screw members) 56a, 56b, 56c, and 56d are provided inside the wire operation section 52 so as to correspond to the number of the bending directions of the bending section 10 to be operated in the bending manner. Here, four first lead screw bearings 57a, 57b 57c, and 57d are provided in the end plate 53a of the first frame member 53 around the circular hole 55 (only the first screw bearing 57a is shown in FIG. 8). The four first lead screw bearings 57a, 57b 57c, and 57d are disposed at positions corresponding to the drive couplings 31a, 31b, 31c, and 31d of the drive source unit 8B. Similarly, four second lead screw bearings 58a, 58b, 58c, and 58d are provided in the end plate 54a of the second frame member 54 around the circular hole 55 (only the second lead screw bearings 58a and 58b are shown in FIG. 8).

One end sections (end sections on the drive source unit 8B side) of the respective lead screws 56a to 56d are extended from the first lead screw bearings 57a, 57b, 57c, and 57d to an outer side of the end plate 53a and the extended end sections of the screws 56a to 56d are provided with the passive coupling sections 30a, 30b, 30c, and 30d, respectively.

Further, the other end sections (end sections on the insertion section 7 side) of the lead screws 56a to 56d are formed with small-diameter sections 56a2, 56b2, 56c2, and 56d2 smaller in diameter than screw sections 56a1, 56b1, 56c1, and 56d1, respectively. The small-diameter sections 56a2 to 56d2 of the respective lead screws 56a to 56d penetrate the end plate 54a from the second lead screw bearings 58a to 58d of the second frame member 54 to extend outside the end plate 54a. The extended end sections of the small-diameter sections 56a to 56d are fitted with E-rings 60 via washers 59 such that the lead screws 56a to 56d not to fall out to the side of the drive source unit 8B. Thereby, four lead screws 56a, 56b, 56c, and 56d are rotatably supported by the first lead screw bearings 57a, 57b, 57c, and 57d and the second lead screw bearings 58a, 58b, 58c, and 58d in their spin directions, respectively.

Coil springs (biasing members) 61 for biasing the respective lead screws 56a to 56d toward the drive source unit 8B are provided on the small-diameter sections 56a2 to 56d2 of the respective lead screws 56a to 56d in a winding manner. The respective lead screws 56a to 56d are biased by spring forces of the coil springs 61 in a direction in which they are pushed toward the drive source unit 8B.

Four nut members (responding members) 62a, 62b, 62c, and 62d moving in the axial directions of the respective lead screws 56a to 56d according to rotations of the respective lead screws 56a to 56d are provided in the wire operation section 52. The respective nut members 62a to 62d include screw hole sections 62a1, 62b1, 62c1, and 62cd screwed with the screw sections 56a1 to 56d1 of the respective lead screws 56a to 56d and wire connection sections 62a2, 62b2, 62c2, and 62d2 connected to the proximal sections of the wires 14.

Further, U-shaped grooves 62a3, 62b3, 62c3, and 62d3 are formed on end sections of the respective nut members 62a to 62d, respectively. Four rotation restricting rods 63 disposed in parallel with centerline directions of the respective lead screws 56a to 56d are engaged with the U-shaped grooves 62a3 to 62d3 in a state where they have been inserted into the U-shaped grooves 62a3 to 62d3. The respective nut members 62a to 62d are supported to be slidable along engagement sections between the U-shaped grooves 62a3 to 62d3 and the rotation restricting rods 63 in axial directions of the rotation restricting rods 63. Thereby, when the respective nut members 62a to 62d advance or retreat in the axial directions of the respective lead screws 56a to 56d according to rotations of the respective lead screws 56a to 56d, rotations of the respective nut members 62a to 62d about the lead screws 56a to 56d are restricted by the four rotation restricting rods 63.

Slit sections 62a4, 62b4, 62c4, and 62d4 for holding the wires 14 are provided on the wire connection sections 62a2 to 62d2 of the respective nut members 62a to 62d. Wire pins 66 are fixed to end sections of the wires 14 positioned on the side of the drive source unit 8B by soldering or the like. Proximal end sections of the wires 14 are assembled to the respective nut members 62a to 62d by inserting the wires 14 into the slit sections 62a4 to 62d4 of the respective nut members 62a to 62d and fixing the wire retainers 67 to the respective nut members 62a to 62d using adhesive or the like. Thereby, when the respective nut members 62a to 62d move toward the drive source unit 8B, the wire pins 66 contact with end faces of the respective nut members 62a to 62d to pull the wires 14, thereby performing bending operation of the bending section 10.

Slit widths of the slit sections 62a4 to 62d4 of the respective nut members 62a to 62d are set to be slightly larger than outer diameters of the wires 14. Thereby, when the respective nut members 62a to 62d move in the direction of the insertion section 7, slacks of the wires 14 can be absorbed by clearances between the slit sections 62a4 to 62d4 of the respective nut members 62a to 62d and the wires 14.

Next, an operation of the above-mentioned configuration will be explained. The separable-type endoscope 1 according to the embodiment is used in a state that the scope section 8A and the drive source unit 8B have been coupled to each other during use of the separable-type endoscope 1. The coupling end section 16 of the scope section 8A and the coupling end section 18 of the drive source unit 8B are caused to abut on each other at a coupling work time of the scope section 8A and the drive source unit 8B. Four passive coupling sections 30a, 30b, 30c, and 30d on the end face of the coupling end section 16 of the scope section 8A and four drive couplings 31a, 31b, 31c, and 31d on the end face of the coupling end section 18 of the drive source unit 8B are set in a state that the former has been engaged with the latter in a detachable manner.

The passive coupling sections 30a to 30d of the scope section 8A and the drive couplings 31a to 31d of the drive source unit 8B are engaged with each other in a detachable manner in a state that the cross-shaped projecting sections 47 of the passive coupling section 30a have been inserted into the cross-shaped recess sections 46 of the drive couplings 31a at a coupling time of the passive sections 30a to 30d and the drive couplings 31a to 31d. At this time, when the cross-shaped projecting section 47 and the cross-shaped recess section 46 are not aligned with each other during a coupling work between the passive coupling sections 30a to 30d of the scope section 8A and the drive couplings 31a to 31d of the drive source unit 8B, the cross-shaped projecting section 47 abut on peripheral section of the cross-shaped recess sections 46, and for example, the drive coupling 31a is once retreated toward the drive motor 19a. In this state, the coupling end section 16 of the scope section 8A and the coupling end section 18 of the drive source unit 8B are connected to each other. Thereafter, when the position of cross-shaped projecting section 47 and the cross-shaped recess section 46 are aligned with each other according to rotation of the drive motor 19a, the drive coupling cylinder 38 is pushed out in the direction of the passive coupling section 30a by the biasing spring 45 so that the both are connected to each other. Thereby, a driving force of the drive motor 19a in the drive source unit 8B can be transmitted to the scope section 8A via the engagement section between the drive coupling 31a and the passive coupling section 30a.

Further, the respective connection end sections of the light guide fiber 13, the CCD cable 21, the water supply pipe conduit 113, the gas supply pipe conduit 114, the suction pipe conduit 118 and the like on the side of the scope section 8A, and the respective connection end sections of the light guide fiber 13, the CCD cable 21, the water supply pipe conduit 113, the gas supply pipe conduit 114, the suction pipe conduit 118, and the like on the side of the drive source unit 8B are detachably connected to each other.

The scope section 8A and the drive source unit 8B are engaged with each other in a state that the engagement pin 32 of the scope section 8A has been inserted into the cam groove 33a of the drive source unit 8B at a coupling time of the scope section 8A and the drive source unit 8B. In this state, the engagement pin 32 is moved to the lock position at the terminal end of the cam groove 33a by rotating the lock ring 33 by a desired rotating angle, so that the scope section 8A and the drive source unit 8B are locked to each other in a coupled state thereof.

Incidentally, in an initial stage at the coupled time of the scope section 8A and the drive source unit 8B, as shown in FIG. 2, the bending section 10 of the scope section 8A is kept in an approximately straight linear state where it is not bent. At this time, the nut members 62a, 62b, 62c, and 62d of the wire operation section 52 are held at home positions disposed on approximately central positions in movement ranges according to rotations of the respective lead screws 56a to 56d.

Thus, the coupling work of the scope section 8A and the drive source unit 8B is terminated, and the endoscope 1 is used in an assembled state of the scope section 8A and the drive source unit 8B. Movement of the endoscope 1 is controlled during use of the endoscope 1 by operating the hand piece 28 of the operation section 6. That is, the bending section 10 is remotely operated in a bending manner by operating the joystick 29a of the hand piece 28. Further, endoscope operations corresponding to functions of the respective remote switches 29b are performed by operating the remote switches 29b.

The joystick 29a of the hand piece 28 is inclination-operated in a desired operation direction at a bending operation time of the bending section 10. A signal generated according to the inclination operation of the joystick 29a is input to the motor control unit 5. Further, a control signal corresponding to the inclination operation of the joystick 29a is output from the motor control unit 5 at the inclination operation time of the joystick 29a so that at least either one of the drive motors 19a and 19b for up and down bending operations and the drive motors 19c and 19d for left and right bending operations in the drive source unit 8B is driven.

Here, for example, when the joystick 29a is inclination-operated in the up or down operation bending direction, the drive motor 19a and 19b for up and down bending operations are driven. At this time, two drive motors 19a and 19b are rotationally driven in opposite directions to each other, for example. Rotation of the output shaft 36a of one drive motor 19a for up and down bending operations is transmitted to the drive coupling 31a via the universal joint 35. Further, the lead screw 56a is rotationally driven in a spin direction via the fitted section of the drive coupling 31a and the passive coupling section 30a.

According to rotation of the lead screw 56a in the spin direction, the nut member 62a is feeding-driven in the axial direction. At this time, rotation of the nut member 62a about the lead screw 56a is restricted by the rotation restricting rod 63. The nut member 62a advances or retreats in the axial direction of the lead screw 56a according to the rotation of the lead screw 56a.

As described above, at a rotating time of the output shaft 36a of one drive motor 19a, the output shaft 36a of the other drive motor 19b is rotationally driven in the reverse direction. The rotation of the output shaft 36a of the drive motor 19b is transmitted to the drive coupling 31b via the universal joint 35. Further, the lead screw 56b is rotationally driven in the reverse direction to the rotation direction of the lead screw 56a via the fitted section of the drive coupling 31b and the passive coupling section 30b. The nut member 62b is feeding-driven in the axial direction in the reverse direction to the nut member 62a according to the rotation of the reverse spin direction of the lead screw 56b. Thereby, two nut members 62a and 62b advance or retreat in opposite directions to each other by the same distance.

For example, one nut member 62a advances toward the scope section 8A by a fixed distance, while the other nut member 62b retreats toward the drive source unit 8B by the same distance as the advancing distance of the nut member 62a. At this time, the wire 14 is operated in a pulling manner by one nut member 62b (or 62a) moving toward the drive source unit 8B. Thereby, the bending section 10 is operated in the up or down direction in a bending manner by the wire 14 pulled toward the drive source unit 8B.

Incidentally, two drive motors 19c and 19d for left and right bending operations are rotationally driven in opposite directions to each other approximately in the same manner as the case of the up and down bending operations at a driving time of the drive motors 19c and 19d for left and right bending operations, too.

The rotation of the output shaft 36a of one drive motor 19c for left and right bending operations is transmitted to the drive coupling 31c via the universal joint 35. Further, the lead screw 56c is rotationally driven in a spin direction via the fitted section of the drive coupling 31c and the passive coupling section 30c.

At the rotating time of the output shaft 36a of the drive motor 19c, the output shaft 36a of the other drive motor 19d is rotationally driven in the reverse direction. The rotation of the output shaft 36a of the drive motor 19d is transmitted to the drive coupling 31d via the universal joint 35. Further, the lead screw 56d is rotationally driven in the reverse direction to the rotation of the lead screw 56c via the fitted section of the drive coupling 31d and the passive coupling section 30d. The nut member 62d is feeding-driven in the axial direction in the opposite direction to the nut member 62c according to rotation of the lead screw 56d in the reverse spin direction. Thereby, two nut members 62c and 62d advance and retreat in the opposite directions by the same distance.

For example, one nut member 62c advances toward the scope section 8A by a fixed distance, while the other nut member 62d retreats toward the drive source unit 8B by the same distance as the advancing distance of the nut member 62c. At this time, the wire 14 is operated in a pulling manner by the one nut member 62d (or 62c) moving toward the drive source unit 8B. Thereby, the bending section 10 is operated in the left or right direction in a bending manner by the wire 14 pulled toward the drive source unit 8B.

The distal end configuration section 11 of the insertion section 7 of the scope section 8B can be bent in a desired direction according to combination of the bending operation in the up or right direction and the bending operation in the left or right direction of the bending section 10.

With the abovementioned configuration, the following effects can be achieved. That is, in the embodiment, the separable-type endoscope 1 where the scope section 8A provided with the slender insertion section 7 that is constituted to be inserted into a body cavity and the drive source unit 8B are detachably coupled to each other is provided. Here, the lead screws 56a, 56b, 56c, and 56d and the nut members 62a, 62b, 62c, and 62d screwed to the respective lead screws 56a to 56d are provided on the wire operation section 52 of the scope section 8A, and four passive couplings 30a, 30b, 30c, and 30d corresponding to four directions of up, down, left, and right, respectively are provided on the lead screws 56a to 56d. Four drive motors 19a, 19b, 19c, and 19d of the driving force generating means 19, the drive coupling shafts 37 rotationally driven in the spin direction by driving forces from the respective drive motors 19a to 19d of the driving force generating means 19, and the drive couplings 31a, 31b, 31c, and 31d are provided in the drive source unit 8B. Driving forces from the respective drive motors 19a to 19d of the driving force generating means 19 are transmitted to the passive coupling sections 30a, 30b, 30c, and 30d via the drive couplings 31a, 31b, 31c, and 31d during coupling between the drive source unit 8B and the wire operation section 52 to rotationally drive the lead screws 56a to 56d in the spin directions. Thereby, the bending section 10 is operated in the up or down direction or in the left or right direction by moving the nut members 62a, 62b, 62c, and 62d in the axial directions and pulling the wires 14 by the nut members 62a (or 62b) and 62c (or 62d) moving toward the drive source unit 8B. Thus, in the embodiment, since the drive mechanism of the lead screw system is used as the drive mechanism for operating the bending section 10 in the bending manner, a high reduction gear ratio can be obtained with a configuration simpler than that of a reduction gear mechanism using a gear train. As a result, such an effect can be obtained that size reduction of the drive side gear reduction mechanism is facilitated, which results in contribution to size reduction as the whole apparatus.

Further, the transmission section of a driving force between the scope section 8A and the drive source unit 8B of the embodiment is coaxial connection and the drive couplings 31a, 31b, 31c, and 31d can retreat in the directions of the respective drive motors 19a to 19d. Therefore, when the positions of the cross-shaped projecting section 47 and the cross-shaped recess section 46 is not aligned with each other at a connecting time of the drive coupling 31a and the passive coupling section 30a, the coupling end section 16 of the scope section 8A and the coupling end section 18 of the drive source unit 8B are connected to each other in a state that the drive coupling 31a has been once retreated toward the drive motor 19a, and when the positions of the cross-shaped projecting section 47 and the cross-shaped recess section 46 are aligned with each other according to rotation of the drive motor 19a following thereafter, the drive coupling cylinder 38 is pushed out in a direction of the passive coupling section 30a by the biasing spring 45 so that both the members are connected to each other. As a result, such an effect can be obtained that the coupling end section 18 of the drive source unit 8B and the coupling end section 16 of the scope section 8 can be connected to each other easily without regard for positioning between the cross-shaped recess sections 46 of the drive couplings 31a, 31b, 31c, and 31d and the cross-shaped projecting sections 47 of the passive coupling sections 30a, 30b, 30c, and 30d.

In the embodiment, therefore, the coupling section between the scope section 8A and the drive source unit 8B in the endoscope 1 can be reduced in size as compared with the conventional one, and attachment and detachment in the coupling section between the scope section 8A and the drive source unit 8B can be performed easily.

Further, in the embodiment, since the lead screws 56a, 56b, 56c, and 56d are used as the drive mechanism for operating the bending section 10 in a bending manner, even if power supply to the bending drive means is stopped after the distal end section has been bent in a desired direction according to a bending operation, the bent state can be maintained. Therefore, an easily-operable configuration can be obtained and economical merit can further be obtained because power for holding the bent state of the bending section 10 is not required.

Figure 10:
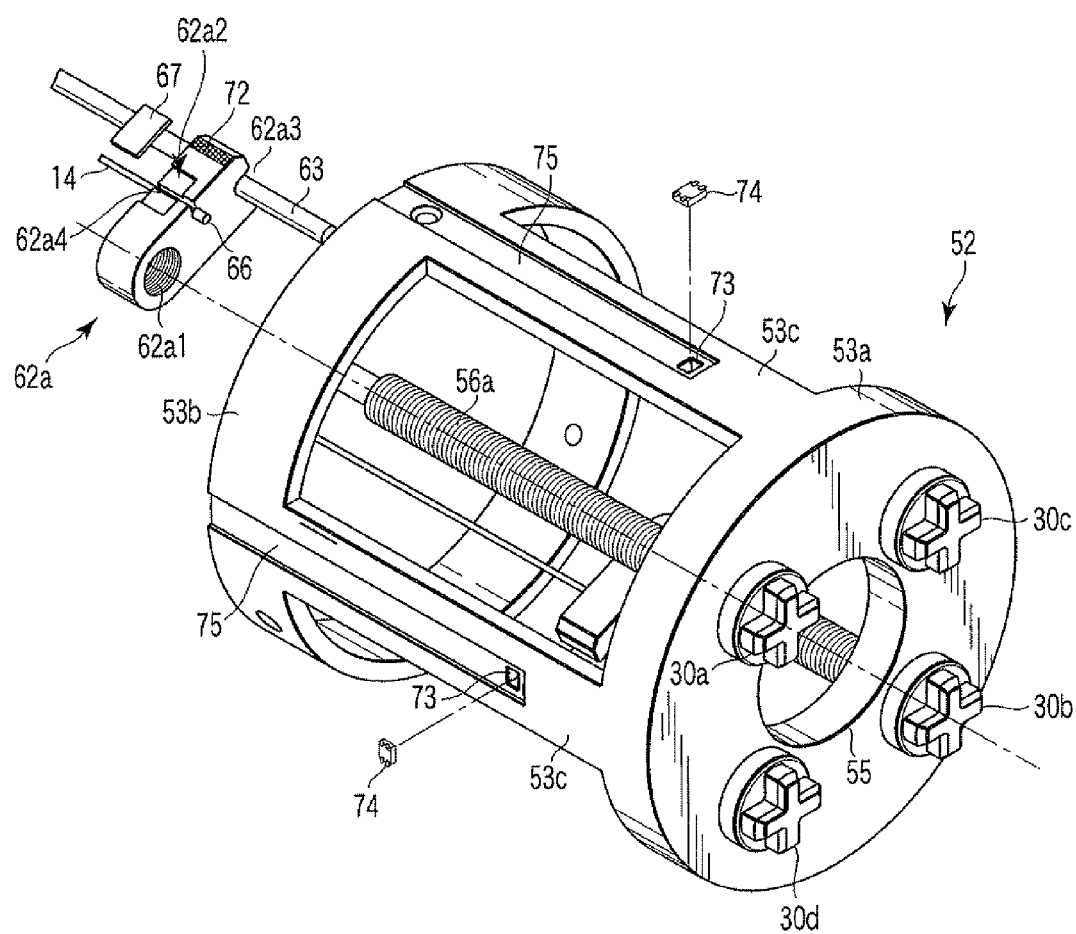
FIG. 10 is a perspective view of a main section showing an internal structure of a large-diameter section of a scope section in the separable-type endoscope according to the second embodiment.
Figure 11:
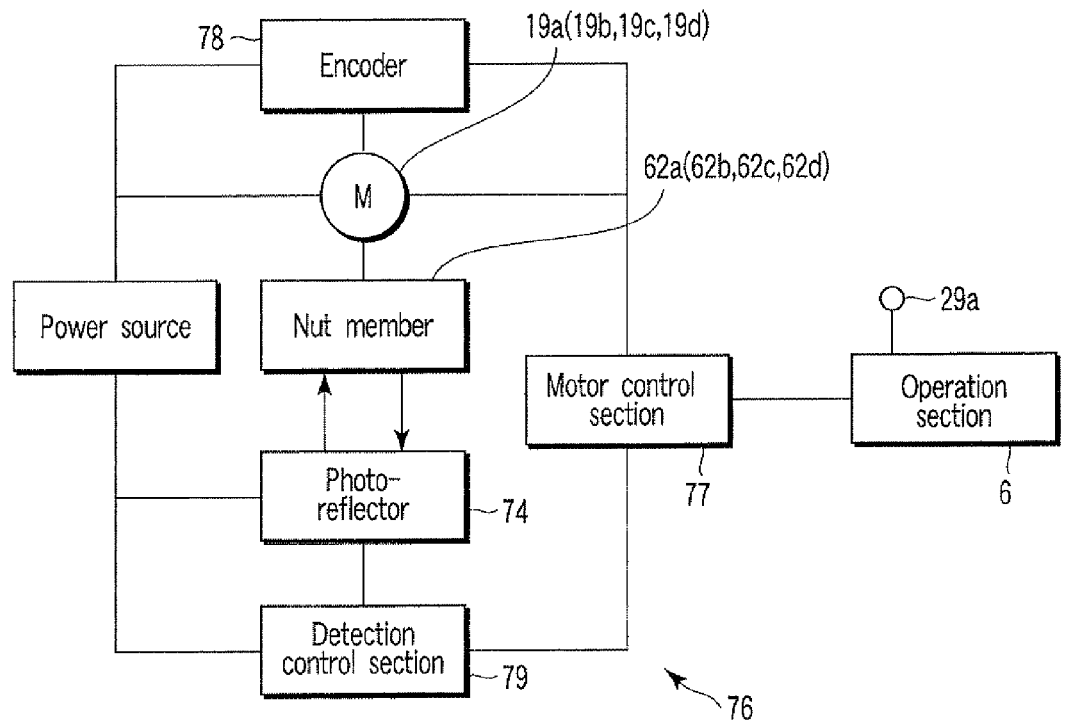
FIG. 11 is a schematic configuration diagram of a control circuit in the separable-type endoscope according to the second embodiment.

FIGS. 9 to 11 show a second embodiment of the present invention. The present embodiment has such a configuration that position detecting means 71 for detecting positions of the respective nut members 62a to 62d are provided in the wire operating section 52 incorporated in the large-diameter section 15 of the scope section 8A in the endoscope 1 of a separable type according to the first embodiment (see FIGS. 1 to 8). Incidentally, the other configurations of the endoscope according to this embodiment are the same as those of the endoscope 1 of a separable type according to the first embodiment, where same sections as those of the endoscope 1 of a separable type according to the first embodiment are attached with same reference numbers and explanation thereof is here omitted.

The position detecting means 71 for the respective nut members 62a to 62d are configured in the following manner. That is, as shown in FIG. 10, reflecting members 72 made of, for example, an aluminum foil tape or the like are provided near the U-shaped grooves 62a3 to 62d3 of the respective nut members 62a to 62d. The reflecting member 72 is disposed on a face opposed to the coupling frame 53c of the first frame member 53.

Further, photo-reflector mounting holes 73 are formed in the coupling frames 53c of the first frame member 53. Photo-reflectors 74 connected to a flexible substrate or the like are assembled to the photo-reflector mounting holes 73. Incidentally, groove sections 75 are provided in the coupling frame 53c to extend along a centerline direction of the first frame member 53. Wiring members (flexible substrates) (not shown) for the photo-reflector 74 are wired in the groove sections 75.

FIG. 11 shows a control circuit 76 assembled in a motor control unit 5 of the separable-type endoscope 1 according to the present embodiment. The control circuit 76 is provided with a motor control section 77 connected to an operation section 6. The motor control section 77 is connected with the respective drive motors 19a to 19d.

Encoders 78 for detecting a rotation angle are respectively provided on the respective drive motors 19a to 19d. Further, the photo-reflectors 74 for detecting positions of the respective nut members 62a to 62d are connected to a detection control section 79. The encoders 78 of the respective drive motors 19a to 19d and the detection control section 79 for the photo-reflectors 74 are connected to the motor control unit 77, respectively.

Rotation angles of the respective drive motors 19a to 19d are detected by the encoders 78 during operation of the respective nut members 62a to 62d. Further, lights emitted from the photo-reflectors 74 when the respective nut members 62a to 62d pass through positions corresponding to the photo-reflectors 74 of the coupling frames 53c are reflected by the reflecting members 72, so that positions of the respective nut members 62a to 62d, for example, an initial position such as a neutral position where the bending angle of the bending section 10 is 0° can be detected. After detection signals from the photo-reflectors 74 are input to the detection control section 79, they are output to the motor control section 77. Thereby, a bending angle of the bending section 10 can be controlled with a high accuracy by the motor control section 77.

In the embodiment, therefore, since the drive mechanism of the lead screw system is used as the drive mechanism for operating the bending section 10 in the bending manner, a high reduction gear ratio can be obtained with a configuration simpler than that of a reduction gear mechanism using a gear train like the first embodiment. As a result, such an effect can be obtained that size reduction of the drive side gear reduction mechanism is facilitated, which can result in contribution to size reduction as the whole apparatus. The coupling section between the scope section 8A and the drive source unit 8B in the endoscope 1 can be reduced in size as compared with the conventional one, and attachment and detachment in the coupling section between the scope section 8A and the drive source unit 8B can be performed easily.

Further, in the embodiment, since the position detecting means 71 for detecting positions of the respective nut members 62a to 62d are provided in the wire operation section 52, such an effect can be obtained that a bending angle of the bending section 10 can be controlled with a high accuracy by the motor control section 77.

Figure 12:
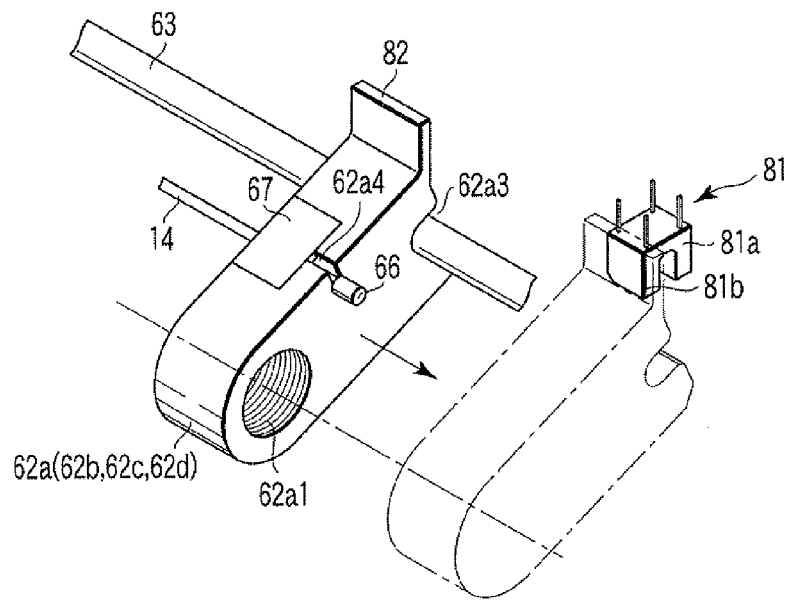
FIG. 12 is a perspective view of a main section showing an initial position detecting mechanism in a separable-type endoscope according to a third embodiment of the present invention.

FIG. 12 shows a third embodiment of the present invention. In the second embodiment (see FIGS. 9 to 11), the configuration where the photo-reflectors 74 detecting positions of the reflecting members 72 of the nut members 62a to 62d are provided in the wire operation section 52 as the position detecting means 71 for detecting positions of the respective nut members 62a to 62d has been shown, but position detecting means 71 having a configuration different from that of the second embodiment is provided in the present embodiment.

That is, in the present embodiment, photo-interrupters 81 including a light emitting section 81a and a light receiving section 81b are provided on the coupling frames 53c of the first frame member 53, as shown in FIG. 12. Further, projecting sections 82 arranged so as to cross between the light emitting section 81a and the light receiving section 81b of the photo-interrupter 81 are provided on the nut members 62a to 62d.

Lights between the light emitting sections 81a and the light receiving sections 81b of the photo-interrupters 81 of the coupling frames 53c are interrupted by the projecting sections 82 of the respective nut members 62a to 62d when the projecting sections 82 crosses between the light emitting sections 81a and the light receiving sections 81b of the photo-interrupters 81 so that positions of the respective nut members 62a to 62d, for example, an initial position such as a neutral position where the bending angle of the bending section 10 is 0° can be detected. In the embodiment, therefore, such an effect can be obtained that the bending angle of the bending section 10 can be controlled with a high accuracy by the motor control section 77 similarly to the second embodiment of the present invention.

Figure 13:
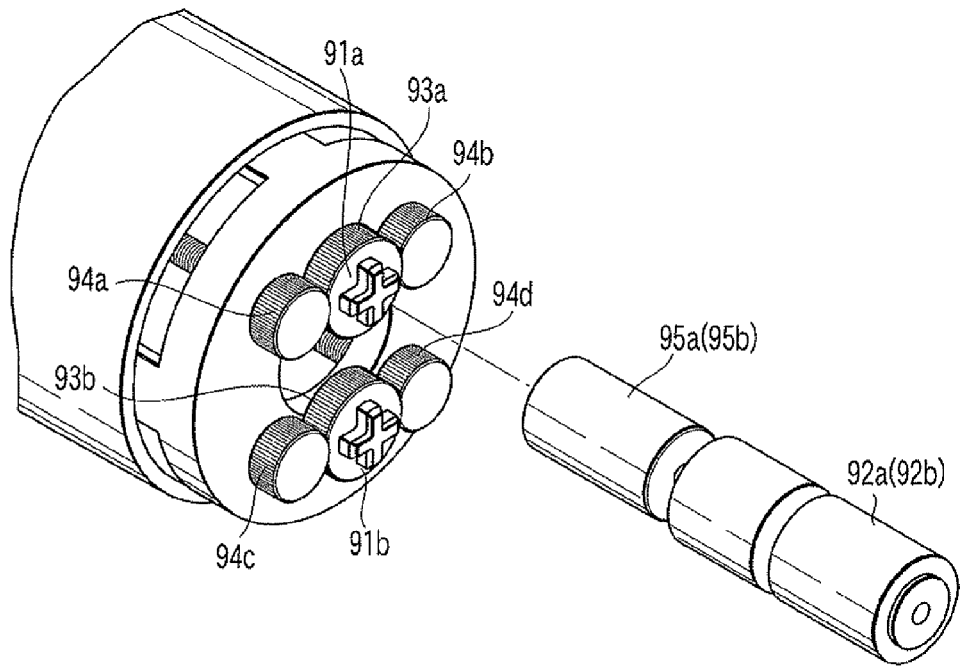
FIG. 13 is a perspective view showing a coupling section between a proximal end side coupling section of a scope section and a drive source unit in a separable-type endoscope according to a fourth embodiment of the present invention.

FIG. 13 shows a fourth embodiment of the present invention. The present embodiment has a configuration that a configuration of the wire operation section 52 incorporated into the large-diameter section 15 of the scope section 8A in the separable-type endoscope 1 according to the first embodiment (see FIGS. 1 to 8) has been modified in the following manner. Incidentally, the other configurations of the endoscope according to this embodiment are the same as those of the endoscope 1 of a separable type according to the first embodiment, where same sections as those of the endoscope 1 of a separable type according to the first embodiment are attached with same reference numbers and explanation thereof is here omitted.

That is, in the wire operation section 52 according to the first embodiment, a configuration that four passive coupling sections 30a, 30b, 30c, and 30d corresponding to the four bending directions of up, down, left, and right are provided on the end face of the coupling end section 16 of the scope section 8A and the four-direction drive motors 19a, 19b, 19c, and 19d for performing bending operations in four directions of up, down, left, and right are respectively provided in the drive source unit 8B is shown. On the other hand, in the wire operation section 52 in the present embodiment, such a configuration is adopted that only one passive coupling section 91a is provided corresponding to bending directions of up and down and only one passive coupling section 91a is provided corresponding to bending directions of left and right on the end face of the coupling end section 16 of the scope section 8A, and only one drive motor 92a is provided corresponding to bending directions of up and down directions and only one drive motor 92b is provided corresponding to bending directions of left and right directions in the drive source unit 8B.

Further, in the wire operation section 52 in the present embodiment, a drive gear 93a and a drive gear 93b are respectively provided in the passive coupling section 91a for up and down directions and the passive coupling section 91b for left and right directions.

Gears 94a to 94d are provided on end sections of four lead screws 56a to 56d on the side of the drive source unit 8B, respectively. Here, the gears 94a and 94b of the lead screws 56a and 56b for bending operation for up and down directions mesh with the drive gear 93a of the passive coupling section 91a for up and down directions, while the gears 94c and 94d of the lead screws 56c and 56d for bending operation for left and right directions mesh with the drive gear 93b of the passive coupling section 91b for left and right directions. Incidentally, the lead screws 56a and 56b for an up direction and for a down direction are threaded in opposite directions to each other (for example, the lead screw 56a for the up direction is a right screw, while the lead screw 56b for the down direction is a left screw). Regarding the left and right directions, similarly, the lead screw 56c for the left direction comprises a right screw and the lead screw 56d for the right direction comprises a left screw.

Further, a drive coupling 95a of the drive motor 92a for bending directions of up and down and a drive coupling 95b of the drive motor 92b for bending directions of left and right are provided in the drive source unit 8B. The drive coupling 95a for bending directions of up and down and the passive coupling section 91a for up and down directions are coupled and the drive coupling 95b for left and right directions and the passive coupling section 91b for left and right directions are coupled at a coupling time of the coupling end section 16 of the scope section 8A and the coupling end section 18 of the drive source unit 8B. Thereby, a driving force can be transmitted with one drive source (drive motor 92a or 92b) for each of the bending operation for up or down direction and the bending operation for left or right direction. Therefore, even when bending for four directions of up, down, left, and right is operated, the operation can be performed by two drive sources (the drive motors 92a and 92b), which results in contribution to size reduction.

According to the present embodiment, therefore, the number of parts can be reduced as compared with the first embodiment, so that such an effect can be obtained that an inexpensive scope section 8A of a separable-type endoscope 1 with a simpler configuration can be provided.

Incidentally, the present invention is not limited to the abovementioned embodiments. For example, in the respective embodiments, the four-direction bending has been explained as an example, but the present invention can be similarly applied to an endoscope for two-direction bending, of course. Further, such a configuration may be adopted that pipe conduits such as the procedure tool insertion pipe conduit 112, the water supply pipe conduit 113, the gas supply pipe conduit 114, and the like inside the insertion section 7 of the scope section BA in the first embodiment are eliminated.

Figure 14A:
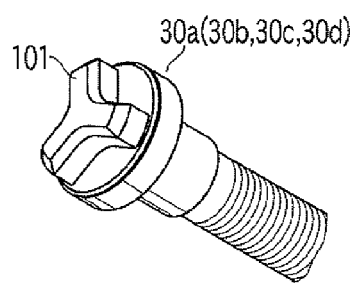
FIG. 14A is a perspective view showing a first modification example of a passive coupling section of a separable-type endoscope of the present invention.
Figure 14B:
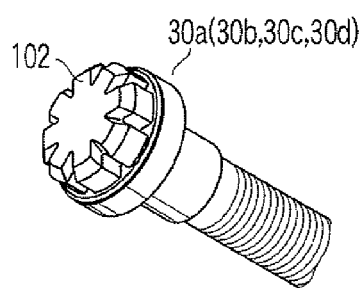
FIG. 14B is a perspective view showing a second modification example of the passive coupling section.

In the respective embodiments, the configuration that the cross-shaped recess section 46 of the drive coupling 31a and the cross-shaped projecting section 47 of the passive coupling section 30a are coupled to each other has been shown, but such a configuration may be adopted that Y-shaped projecting sections 101 with an approximately Y shape are provided on the passive coupling sections 30a to 30d like a first modification shown in FIG. 14A or non-circular engagement projections such as a polygonal projecting section 102 obtained by combining two cross-shaped projecting sections are provided thereon like a second modification shown in FIG. 14B, and engagement recess sections including a shape analogous to the Y-shaped projecting section 101 or the polygonal projecting section 102 is provided on the drive coupling 31a. Further, the present invention can be implemented in various manners modified without departing from the gist of the present invention.

INDUSTRIAL APPLICABILITY

The present invention is effective in a technical field using an endoscope of a drive source unit separable type where a drive source unit in which driving force generating means for operating a bending section which is disposed on a distal end of an insertion section of the endoscope in a bending manner is incorporated is detachably coupled to a proximal end section of the insertion section via a separable section or a technical field manufacturing the endoscope.

What is claimed is:
1. An endoscope comprising:
a scope section which includes a distal end section, a proximal end section and a central axis defined by the distal end section and the proximal end section and which is configured to be inserted into a body cavity;
a drive source unit which is separably coupled to the proximal end section of the scope section, wherein:
the scope section includes:
a bending section which is configured by coupling a plurality of bending pieces,
a coupling end section which is separably coupled to the drive source unit at the proximal end section of the scope section,
a wire which is configured to operate the bending section in a bending manner and which includes a distal end section, a proximal end section and a longitudinal axis defined by the distal end section and the proximal end section of the wire and configured to be parallel with the central axis of the scope section, where the distal end section of the wire extends toward the distal end section of the scope section and the proximal end section of the wire extends toward the proximal end section of the scope section, and
a wire operation section which is connected to the proximal end section of the wire and which is provided on the coupling end section, the wire operation section including:
a screw member including a distal end section,
a proximal end section and a rotation axis parallel with the longitudinal axis of the wire and rotatably supported around the rotation axis on the coupling end section,
a passive coupling section provided at the proximal end section of the screw member, and
a responding member which includes a screw hole section screwed with the screw member, which is connected to the proximal end section of the wire and which is configured to move in the longitudinal axis of the wire according to rotation of the screw member; and
the drive source unit includes:
a driving force generating portion which is configured to generate a driving force to bend the bending section,
a drive shaft body which includes a distal end section and a proximal end section connected to the driving force generating portion, and which is configured to be rotated by the driving force from the driving force generating portion, and
a drive coupling portion which is disposed at the distal end section of the drive shaft body, which is configured to be separably coupled to the passive coupling portion of the wire operation section, and which is configured to transmit the driving force from the driving force generating portion to the screw member through the drive shaft body, the drive coupling portion and the passive coupling portion and configured to move the responding member and the wire when the drive coupling portion of the drive source unit is coupled with the passive coupling portion of the wire operation section.

2. The endoscope according to claim 1, wherein
the bending section is configured to be operable in four directions of up, down, left, and right in a bending manner, and
the wire includes a pair of up and down direction wires for up and down bending operations configured to operate the bending section in up and down directions and a pair of left and right direction wires for left and right bending operations configured to operate the bending section in left and right directions.

3. The endoscope according to claim 2, wherein a set of two of the screw members configured to operate the up and down direction wires and a set of two of the screw members configured to operate the left and right direction wires are each driven by one drive source.

4. The endoscope according to claim 3, wherein
the screw member includes a gear section provided on the proximal end section of the scope section so as to be exposed from the coupling end section;
the coupling end section includes
a first drive gear meshing with the gear section of the set of two of the screw members configured to operate the up and down direction wires,
a second drive gear meshing with the gear section of the set of two of the screw members configured to operate the left and right direction wires;
the passive coupling section is provided on the first drive gear and the second drive gear, respectively; and
each of the drive coupling section is engaged with the passive coupling section of the first drive gear and the passive coupling section of the second drive gear, respectively, to perform transmission of a driving force.

5. The endoscope according to claim 1, wherein at least one of the passive coupling portion of the wire operation section and the drive coupling portion of the drive source unit includes a non-circular engagement projecting section and the other thereof includes an engagement recess section separably engaged with the engagement projecting section.

6. The endoscope according to claim 1, wherein the wire operation section includes a detecting portion configured to detect advance and retreat of the responding member.

7. The endoscope according to claim 4, wherein the detecting portion includes one of a photo-reflector configured to detect a position of a reflecting member provided on the responding member and a photo-interrupter configured to detect a position of a projection provided on the responding member.

8. The endoscope according to claim 1, wherein
the drive coupling section includes a drive coupling shaft and a drive coupling cylinder, and
the drive coupling cylinder includes a biasing spring configured to bias the drive coupling cylinder in a distal end direction thereof interposed between the drive coupling cylinder and the drive coupling shaft.

9. The endoscope according to claim 1, wherein the coupling end section includes a frame configured to support the screw member.

10. The endoscope according to claim 9, wherein
the proximal end portion of the scope section includes a first cylindrical section with a first engagement portion, and
the drive source unit includes a second cylindrical section with a second engagement portion which is configured to engage with the first engagement portion.

\* \* \* \* \*